United States Patent [19]

Charu

[11] Patent Number: 5,914,334
[45] Date of Patent: Jun. 22, 1999

[54] STABLE GEL FORMULATION FOR TOPICAL TREATMENT OF SKIN CONDITIONS

[75] Inventor: Prakash M. Charu, Fullerton, Calif.

[73] Assignee: Allergan, Inc., Irvine, Calif.

[21] Appl. No.: 08/623,184

[22] Filed: Mar. 28, 1996

Related U.S. Application Data

[63] Continuation of application No. 08/255,094, Jun. 7, 1994, abandoned.

[51] Int. Cl.$^6$ .......................... A61K 31/455; A61K 7/48; A61K 9/06; A61K 9/107
[52] U.S. Cl. .......................... 514/337; 514/859; 514/863; 514/886; 514/887; 514/944; 514/964; 514/772.3; 424/400; 424/401; 424/486
[58] Field of Search ........................ 514/337, 859, 514/863, 886, 887, 944, 964, 772.3; 424/400, 401, 486

[56] References Cited

U.S. PATENT DOCUMENTS 4,895,727  1/1990  Allen .................................. 424/642

FOREIGN PATENT DOCUMENTS

90/14833  12/1990  WIPO .

OTHER PUBLICATIONS

DRUGNL Abstract, accession No. 92:626, 1992.
DRUGU Abstract, accession No. 92–37505, 1992.
DRUGU Abstract, accession No. 92–49018, 1992.
DRUGU Abstract, accession No. 93–27556, 1993.
BIOSIS Abstract, accession No. 93:356017, 1993.
DRUGU Abstract, accession No. 93–27551, 1993.
DRUGU Abstract, accession No. 93–27541, 1993.
DRUGU Abstract, accession No. 93–49758, 1993.
BIOSIS Abstract, accession No. 93:356017, 1993.
BIOSIS Abstract, accession No. 93:356010, 1993.
BIOSIS Abstract, accession No. 93:538730, 1993.
BIOSIS Abstract, accesssion No. 92:496186, 1992.
Sefton et al., "AGN 190618, an investigational retinoid gel for the treatment of plaque psoriasis," The Journal of Investigative Dermatology, vol. 101, No. 3, p. 470, item no. 496, Sep. 1993.
Weinstein et al., "New topical retinoid for therapy of psoriasis: dose–ranging study of AGN 190168," The Journal of Investigative Dermatology, vol. 100, No. 4, p. 544, item no. 332, 1993.
Shalita et al., "Double–blind study of AGN 190618, a new retinoid gel, in the topical treatment of acen vulgaris," The Journal of investigative Dermatology, vol. 100, No. 4, p. 542, item no. 325, Apr. 1993.

*Primary Examiner*—John Pak
*Attorney, Agent, or Firm*—Walter A. Hackler

[57] ABSTRACT

The present invention provides a stable gel formulation for topical treatment of skin conditions in humans. The stable gel formulation includes an active agent, having activity for treatment of acne and psoriasis, which is insoluble in water and a plurality of nonaqueous vehicles for both solubilizing said active agent and forming a gel therewith enabling topical application of the gel to a skin condition. The plurality of vehicles are each present in amounts, and in combination, to control release of the active agent from the gel to the skin condition.

8 Claims, 11 Drawing Sheets

STABLE GEL FORMULATION FOR TOPICAL TREATMENT OF SKIN CONDITIONS

This application is a continuation of application Ser. No. 08/255,094, filed Jun. 7, 1994 now abandoned.

The present invention generally relates to pharmaceutical preparations and more specifically relates to stable gels for topical treatment of both acne and psoriasis in humans.

Acne is a relatively common inflammatory disease afflicting the skin. The severity of the disease ranges from a more or less superficial disorder to inflammatory conditions in which bacterial invasions occur causing inflamed and infected sacs to appear. Most activity occurs where sebaceous glands are the largest, most numerous and of course most active. Left untreated, the acne lesions may become extensive and leave permanent disfiguring scars.

The cause of acne is increased activity of the sebaceous glands and the epithelial tissue lining the infundibulum. The increased activity of the sebaceous glands produces more sebum which consists of free and esterified fatty acids as well as unsaponifiable lipid components which results in increased skin oiliness.

In inflammatory acne, the initial inflammation of hair follicle walls results from the presence of free fatty acids derived from the sebum. In the presence of bacterial lipolytic enzymes, triglycerides of the sebum are split, releasing the fatty acids. The normal bacterial flora in the sebaceous duct produce the enzymes responsible for splitting the triglycerides.

Current treatments for acne include cymedolytics, exfoliants, oral and topical bacteriostatics, as well as systemic antibiotics. Ideally, topical formulations for the treatment of acne should be compounded with little or no oil in the formulation and should not leave any oil film on the skin to compound the condition.

Psoriasis, on the other hand, is a chronic, hereditary, recurrent papulosquamous dermatosis typically involving the scalp and extensor surfaces of the limbs, especially the elbows, knees and shins. The distinctive lesion of psoriasis is a vivid red macule, papule or plaque covered almost to its edge by silvery lamellated scales. Psoriasis is further characterized by accelerated epidermal proliferation, leading to excessive scaling of the skin due to the fact that psoriatic skin loses water eight to ten times faster than normal skin. For this reason, topical treatment thereto typically contains oils which are best suited for moisturizing the skin.

The present invention is directed to a formulation and a method of producing a formulation in gel form that does not contain any oil and therefore meets the requirements of treatment and also offers a high moisturizing factor for psoriatic treatment. Effectiveness of an active agent for treatment of acne and psoriasis is, of course, dependent upon the availability of the agent for affected areas when applied in a topical manner. That is, the formulation must not only incorporate sufficient active agent to properly treat the condition but also the release of the active agent from the formulation is an absolute necessity.

In accordance with the present invention, a gel formulation has been developed which is suitable for treatment of both acne and psoriasis which incorporates vehicles for both solubilizing the active agent and for controlling release of the active agent from the gel to the skin condition.

SUMMARY OF THE INVENTION

In accordance with the present invention, a stable gel formulation for topical treatment of skin conditions in humans is used as an active agent having activity for treatment of acne and psoriasis and is insoluble in water. In combination therewith is a plurality of nonaqueous vehicles for both solubilizing the active agent and forming a gel therewith. The nonaqueous vehicles enable topical application of the gel to a skin condition with the vehicles each being present in amounts, in combination, to control the release of the active agent from the gel to the skin condition.

Other combinations of the vehicles provide a means to maximize the solubility of the active agent in the gel.

More particularly, the formulation comprises three vehicles and the active agents comprises a synthetic retinoid, preferably Ethyl-6-[2-(4,4-dimethylthiochroman-6-yl)-ethynyl]nicotinate or any of the other synthetic retinoids disclosed in U.S. Pat. Nos. 4,739,098; 4,923,884; 4,810,804; 5,013,744; 4,895,868; 5,006,550; 4,992,468; 5,149,705; 5,202,471; 5,130,335; and 5,134,159, these patents being incorporated into the present application by this specific reference thereto.

Vehicles are used to both solubilize the active agent and form a gel and preferably comprise Polysorbate 40 (a polyhydroxy organic compound), Poloxamer 407 and Hexylene glycol.

More specifically, the present invention provides a stable gel formulation having an effective amount of a compound having the formula: Ethyl-6-[2-(4,4-dimethylthiochroman-6-yl)-ethynyl]nicotinate (sometimes hereinafter referered to as AGN) for treating acne in a pharmaceutical carrier comprising water, edetate disodium, ascorbic acid, Carbomer 934P, Poloxamer 407, polyethylene glycol, Polysorbate 40, hexylene glycol, butylated hydroxytoluene, butylated hydroxyanisole, benzyl alcohol, and tromethamine.

A method in accordance with the present invention for preparing a formulation for topical treatment of both acne and psoriasis includes the steps of mixing purified water, edetate disodium, ascorbic acid and Carbomer 934P (a polyacrylic acid) until the carbomer is dispersed to form a part I, mixing purified water, Poloxamer 407 to form a part II and adding part II to part I while homogenizing same.

The method further includes mixing polyethylene glycol, Polysorbate 40, hexylene glycol, butylated hydroxytoluene and butylated hydroxyanisole and heating to dissolve same. Thereafter, the heated mixture is cooled to room temperature and benzyl alcohol and Ethyl-6-[2-(4,4-dimethylthiochroman-6-yl)-ethynyl]nicotinate are added thereto to form a part III.

Purified water is mixed with tromethamine to form part IV and part III is added to parts I and II while stirring before part IV with mixing until homogeneous.

BRIEF DESCRIPTION OF THE DRAWINGS

The advantages and features of the present invention will be better understood by the following description when considered in conjunction with the accompanying drawings indicated as follows.

DETAILED DESCRIPTION

Figure 1:
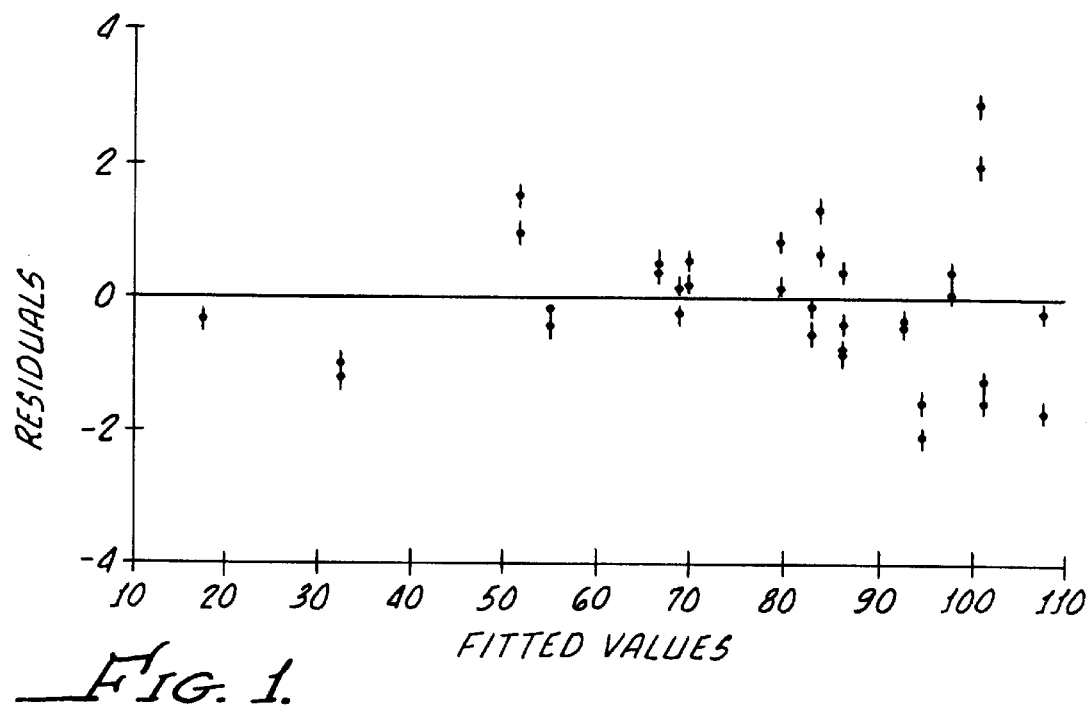
FIG. 1: Plot of residuals vs. fitted values for the solubility data.

The following factors must be taken into consideration in the formulation of a suitable pharmaceutical preparation for the treatment of acne and psoriasis:

Formulation and Patient Compliance Issues

Nonirritating and nonstaining

Odor-free

Nonoily and nondrying

Water washable

Easy application and storage

Ingredient labeling

Formulation Issues

Development of only one formula for both acne and psoriasis

Local drug delivery and little systemic effect

Ease of scaleup

Stability for a minimum of two years

Use of safe and compendial excipients

Paraben-free formulation

Propylene glycol-free formulation

Drug having minimal affinity for the base

Alcohol-free formulation

Oil-free formulation

Formula showing minimal placebo effect

Some portion of drug in solution for immediate release

Irritation levels comparable to other marketed retinoids

It has been found that the compound Ethyl-6-[2-(4,4-dimethylthiochroman-6-yl)-ethynyl]nicotinate is active in the treatment of acne and psoriasis. However, the solubility of AGN 190168 in water is extremely low. The solubility of Ethyl-6-[2-(4,4-dimethylthiochroman-6-yl)-ethynyl] nicotinate in various solutions at 35°±0.5° C. is shown in Table I.

TABLE I

Solubility of AGN in Various Aqueous Solutions at 35° ± 0.5° C.

| Aqueous Mixtures (v/v) | Avg. Solubility (mg/ml) |
|---|---|
| 100% Water | Not Detected |
| 20% Ethanol/Water | Not Detected |
| 40% Ethanol/Water | 0.1472 ± 0.0209 |
| 60%.Ethanol/Water | 2.2235 ± 0.000780% |
| 40% Ethanol/Water | 0.1472 ± 0.0209 |
| 80% Ethanol/Water | 8.2248 ± 0.2206 |
| 20% PEG-400/Water | Not Detected |
| 40% PEG-400/Water | 0.0044 ± 0.0005 |
| 60% PEG-400/Water | 0.0896 ± 0.0011 |
| 80% PEG-400/Water | 2.1628 ± 0.0899 |
| 1% Oleth-20/Water | 0.0733 ± 0.0030 |
| 2% Oleth-20/Water | 0.1492 ± 0.0006 |
| 4% Oleth-20/Water | 0.3112 ± 0.007 |
| 96% Oleth-20/Water | 0.4352 ± 0.0011 |
| 0.07% Polysorbate 40 | 0.0037 ± 0.0006 |
| 0.15% Polysorbate 40 | 0.0092 ± 0.0014 |
| 0.30% Polysorbate 40 | 0.0183 ± 0.0018 |
| 0.50% Polysorbate 40 | 0.0332 ± 0.0003 |

As hereinabove noted, a solution dosage form containing AGN is not desirable in view of the aqueous content, the difficulty in handling the solution, and application to skin. A cream formulation is feasible but the oil utilized therein is also not suitable for acne treatment as hereinabove noted.

The formulation in accordance with the present invention includes a number of ingredients as set forth in Table II.

TABLE II

Ingredients Used in Formulation of an AGN Gel

| INGREDIENT | FUNCTION |
|---|---|
| AGN | Drug |
| Purified water | Excipient |
| Edetate Disodium | Stabilizer |
| Ascorbic acid | Stabilizer |
| Carbomer 934P | Thickening agent |
| Poloxamer 407 | Surfactant |
| PEG-400 | Co-solvent |
| Polysorbate 40 | Surfactant |
| Hexylene glycol | Co-solvent |
| Butylated hydroxytoluene | Stabilizer |
| Butylated hydroxyanisole | Stabilizer |
| Benzyl alcohol | Preservative |
| Triethanolamine/ Tromethamine | Neutralizer |

Rationale for Selection of Excipients

The rationale for selecting the excipients used in the AGN topical gel is outlined below.

PEG 400: Polyethylene glycol 400 is used in AGN topical gel formulation as a solvent to solubilize the active drug, AGN. Solubility of AGN in PEG 400 is 2.2 mg/mL. At ambient conditions PEG 400 is a liquid which is completely miscible with water, and the topical formulations can be compounded easily. PEG 400 is chemically stable and does not support microbial growth. PEG 400 is hygroscopic and topical formulations prepared with PEG 400 do not dry on skin readily after application. The following marketed Rx products in USA contain PEG 400 as excipient: Retin A Liquid®, Lotrimin® solution®, Cleocin T® gel, Halotex® 1% Cream, Halog® 0.1% ointment, and Mycelex® solution. PEG 400 is a component of "Polyethylene glycol ointment NF".

Carbomer 934P is used as a viscosity builder in AGN topical gel formulations. Carbomer 934P has the ability to produce high viscosities at low concentration after neutralization, with much greater lot to lot consistency than the natural gums and does not support microbial growth. Carbomer 934P gels show good plastic flow properties, having a significant yield value (commonly defined as initial resistance to flow under applied stress). AGN topical gel, prepared with carbomer 934P, shows acceptable thickness and spreads evenly on application to the skin.

Edetate disodium is used in AGN topical gels as a chelating agent for the stabilization of the overall formulation. Trace amounts of iron and other transition metals are known to degrade carbopol resins (used as a thickener) and PEG 400 (used as solvent) in AGN gel. Edetate disodium is used to sequester traces of metal ions which would catalyze oxidation of AGN and ascorbic acid used in the formulation. Aqueous solutions of Polysorbate 40 are known to undergo autoxidation as well.

Polysorbate 40 is used as surfactant to solubilize the AGN. Polysorbate 40 is liquid at ambient conditions and miscible with PEG 400-water mixtures and does not cloud the solution. Polysorbate 40 has an HLB value of 15.6 and this high HLB value surfactant is selected to solubilize AGN in PEG 400.

Poloxamer 407 is used as a surfactant in the water phase of the AGN gel formulation. Poloxamer 407 is water soluble and has an HLB value of 20.

Hexylene glycol is miscible with water-PEG 400 mixtures and is used as a cosolvent to solubilize AGN along with PEG 400.

Tromethamine is used to neutralize Carbomer 934P and as a pH adjuster while manufacturing AGN topical gel.

Ascorbic acid is used as an antioxidant and is added to the water phase while manufacturing AGN topical gel. Laboratory formulation of AGN prepared without ascorbic acid shows poor stability.

Benzyl alcohol is used along with PEG 400 and Polysorbate 40 to solubilize the active AGN. Benzyl alcohol is also used as preservative.

Butylated hydroxytoluene, butylated hydroxyanisole are used in the AGN topical gel formulation as antioxidants protecting the overall product from residual peroxides found in excipients. These antioxidants are not water soluble and are added to the PEG 400 phase while manufacturing. Alcoholic solutions containing AGN are stabilized by BHT (preformulation report).

Nitrogen, as inert gas, is used while manufacturing AGN topical gel to reduce any potential for autoxidation of the active ingredient and other excipients.

Purified Water is used as the vehicle in the AGN topical gel formulation.

Typical concentration of each ingredient in the gel is shown in Table III.

TABLE III

Concentration (% W/W) of ingredients in the 0.1% AGN Tropical Gel (Formula 8606X)

| INGREDIENT | FUNCTION | CONCENTRATION % W/W |
|---|---|---|
| AGN | Drug | 0.1 |
| Purified water | Excipient | 49.25 |
| Edetate Disodium | Stabilizer | 0.05 |
| Ascorbic acid | Stabilizer | 0.05 |
| Carbomer 934P | Thickening agent | 1.25 |

TABLE III-continued

Concentration (% W/W) of ingredients in the 0.1% AGN Tropical Gel (Formula 8606X)

| INGREDIENT | FUNCTION | CONCENTRATION % W/W |
|---|---|---|
| Poloxamer 407 | Surfactant | 0.2 |
| PEG-400 | Co-solvent | 45.0 |
| Polysorbate 40 | Surfactant | 0.2 |
| Hexylene glycol | Co-solvent | 2.0 |
| Butylated hydroxytoluene | Stabilizer | 0.05 |
| Butylated hydroxyanisole | Stabilizer | 0.05 |
| Benzyl alcohol | Preservative | 1.0 |
| Triethanolamine/ Tromethamine | Neutralizer | 0.8 |

The ingredients are combined together to make the following four parts:

| INGREDIENT | FUNCTION |
|---|---|
| Part I: | |
| Purified water | Excipient |
| Edetate Disodium | Stabilizer |
| Ascorbic acid | Stabilizer |
| Carbomer 934P | Thickening agent |
| Part II: | |
| Purified water | Excipient |
| Poloxamer 407 | Surfactant |
| Part III: | |
| PEG-400 | Co-solvent |
| Polysorbate 40 | Surfactant |
| Hexylene glycol | Co-solvent |
| Butylated hydroxytoluene | Stabilizer |
| Butylated hydroxyanisole | Stabilizer |
| Benzyl alcohol | Preservative |
| AGN | Drug |
| Part IV: | |
| Purified water | Excipient |
| Tromethamine | Neutralizer |

Procedure for Preparing the Gel

The procedure for preparation of the gel is as follows:

1. The ingredients in part I are mixed with low speed homogenization until the carbomer is dispersed.

2. The ingredients in part II are mixed.

3. Part II is added to part I and the mixture is homogenized.

4. The first four ingredients in part III are combined and heated to 65 degrees Centegrade until all compounds are dissolved.

5. The mixture is allowed to cool to room temperature. Then benzyl alcohol and the drug are slowly combined while mixing (in the yellow room).

6. Part III is added to Part I/II while stirred using a low speed homogenizer.

7. The ingredients in part IV are combined and added to the above mixture and mixed until homogeneous.

It has been found that three vehicles influenced drug solubility and release; namely, polysorbate 40, poloxamer 407, and hexylene glycol. Using experimental design, variations of the gel were formulated which contained polysorbate 40 and poloxamer 407, each at three levels, and hexylene glycol at two levels. Based on this 2×3² factorial design, eighteen variations of the gel were formulated and the effect of surfactant and co-solvent concentration on drug solubility and in vitro release were evaluated.

Materials

Ethyl-6-[2-(4,4-dimethylthiochroman-6-yl)-ethynyl] nicotinate (available from SK&F, Cambridge), Ascorbic acid, USP (Hoffman-La Roche), Benzyl alcohol, NF (Akzo), Butylated hydroxyanisole, NF (Penta), Butylated hydroxytoluene, NF (Penta), Carbomer 934P, NF (Carbopol 974P, B.F. Goodrich), Edetate Disodium, USP (Akzo), Ethyl alcohol (Quantum Chemical Corp.), Hexylene glycol, NF (Union Carbide), Poloxamer 407, NF (BASF), Polyethylene glycol 400, NF (Union Carbide), Polysorbate 40, NF (ICI), Purified water, USP, Silastic® medical grade sheeting (Dow Corning Wright), Tromethamine, USP, (American Biorganic).

Equipment

Brookfield counter rotating mixer (Brookfield Engineering laboratories Inc.), Nova II Hot plate/stirrer, (Baxter).

Diffusion Apparatus

Cassette® pump drive unit (Manostat), Posi Bloc™ Diffusion cell heater (Crown glass company, Inc.), Retriever IV fraction collector (ISCO, Inc.), Teflon® flow-thru diffusion cells (Crown Glass Company, Inc.).

Chromatography Instrumentation 116 programmable solvent module (Beckman), 166 Detector (Beckman), Beckman Ultrasphere XL HPLC column, 4.6 mm×7.0 cm (Beckman), Auto-injector WISP™ model 712 (Waters).

µVAX® Software

Access Chrome® data collection system (Perkin-Elmer Nelson), RS/Discover® (BBN software).

Methods

Preparation of Experimental Gels

The ingredients used in the prototype gel (formula 8606X) are shown in Table III. Based on experimental design, variations of the prototype gel were prepared which contained different concentrations of three ingredients present in the gel; polysorbate 40 (PS), poloxamer 407 (PX), and hexylene glycol (HG). The purpose was to study the effect of these factors on the release rate and solubility of AGN in the vehicle of the gels. The procedure for the preparation of the gels is described in the formulation record.

Experimental Design

Experimental design was used to determine the number of formulations necessary to provide the desired information in the most efficient way. The variables studied were the concentrations of hexylene glycol, poloxamer 407, and polysorbate 40. Hexylene glycol was studied at 2 levels and each of the surfactants was studied at 3 levels. Therefore, a 2×3² factorial design was produced which required the preparation of 18 formulations. Table IV shows the actual concentrations used for each of these ingredients. For all ingredients, the concentration of 0 indicates that the ingredient is not present.

TABLE IV

The Levels of Poloxamer 407, Polysorbate 40, and Hexylene Glycol Used in the Preparation of Various Experimental Gels

| INGREDIENT | CONCENTRATION (% W/W) | | |
| --- | --- | --- | --- |
| Poloxamer 407 | 0 | 0.2 | 0.4 |
| Polysorbate 40 | 0 | 0.2 | 0.4 |
| Hexylene glycol | 0 | | 2 |

The experimental design is shown in Table V. This design required the preparation of 18 gels containing all possible combinations of the surfactants and co-solvent at the desired levels. Since the prototype gel (gel B) represented one of the gels, it was necessary to formulate 17 other gels.

TABLE V

The 2 × 3² Factorial Design Used to Prepare the Various Experimental Formulations of the Prototype Gel (Gel B)

| Gel | Hexylene Glycol | Polysorbate 40 | Poloxamer 407 |
| --- | --- | --- | --- |
| 10 | 0.0 | 0.0 | 0.0 |
| 11 | 0.0 | 0.0 | 0.4 |
| 8 | 0.0 | 0.0 | 0.2 |
| 12 | 0.0 | 0.4 | 0.0 |
| 18 | 0.0 | 0.4 | 0.4 |
| 15 | 0.0 | 0.4 | 0.2 |
| 9 | 0.0 | 0.2 | 0.0 |
| 16 | 0.0 | 0.2 | 0.4 |
| 7 | 0.0 | 0.2 | 0.2 |
| 3 | 2.0 | 0.0 | 0.0 |
| 5 | 2.0 | 0.0 | 0.4 |
| 1 | 2.0 | 0.0 | 0.2 |
| 6 | 2.0 | 0.4 | 0.0 |
| 17 | 2.0 | 0.4 | 0.4 |
| 14 | 2.0 | 0.4 | 0.2 |
| 2 | 2.0 | 0.2 | 0.0 |
| 13 | 2.0 | 0.2 | 0.4 |
| B | 2.0 | 0.2 | 0.2 |

Solubility of AGN in the Gels

To determine the saturated solubility of the drug in the vehicle of each of the 18 gel formulations, solvent systems containing the same ingredients as the gels were prepared. The saturated solubility was determined once in solutions of the vehicle without carbomer and base, and another time by substituting propionic acid for carbomer in order to ease filtration of the solution while keeping the ionic strength of the solution as close to that of the gel as possible. The solutions were filtered through a 0.45 µm filter to remove any crystals which may have formed. The resulting solutions were then diluted and their drug content was assayed using High Performance Liquid Chromatography (HPLC) as described in Method HL036.

Release of AGN from the Gels

The release of AGN through each of the 0.1% gels was studied using a previously developed release method. The collected fractions were then assayed directly using HPLC Method HL036.

Slopes of the Release Profiles

The data generated from the assay of the collected fractions for each gel were used to plot the release profile of the drug as the % drug released vs. square root of time. For each release profile, the slope of the linear region containing at least 6 points was calculated using linear regression. The standard deviation and correlation coefficient of each slope was also calculated.

Analysis of Solubility and Release Data

The saturated solubility values, and slopes of the line obtained from the plot of % drug released vs. square root of time for each gel were analyzed statistically. The difference between the slopes and solubilities from gel to gel were studied using a two tailed t-test to find the gels which resulted in significantly different values. RS/Discover® was used to calculate equations which fit the data and to construct response surfaces.

Maximizing Solubility and Release

The resulting slope and solubility data were also analyzed using RS/Discover® in order to maximize these responses. Initially the slope was maximized to find the gel exhibiting maximum drug release, then solubility was maximized in order to find the gel which had the highest drug solubility. Finally, both solubility and slope were simultaneously maximized to find the gel which provided optimum drug release and solubility.

Effect of Drug Particle Solubility on Drug Release

From the solubility data it is apparent that approximately 90% of the drug is present in the aqueous based gel in the form of solid particles. In order to determine if the rate of dissolution of the particles is limiting the rate of drug release, the data obtained form the in vitro release study was analyzed.

Effect of Membrane on Drug Release

In order to investigate the possibility of the silicone membrane being rate limiting, the slope of the release profile for drug diffusion through the gel was compared to the slope of the release profile obtained from a saturated solution of the drug.

Effect of Drug Concentration on Release Rate

A release study showing the effect of drug concentration on the in vitro release of AGN from three gel formulations was conducted. The three gels were formula 8606X (0.1%), 8607X (0.05%), and 8649X (0.025%), and plots of amount of drug release vs. square root of time were compared.

Results and Discussion

Solubility of AGN in the Gels

The solubility of the drug was determined in the vehicle of the prototype gel (gel B), and all the other formulated gels in order to investigate the effect of the surfactants and cosolvent addition on drug solubilization in the gel. The solubility values obtained using the two methods (without carbomer and base vs. with propionic acid and base) were not significantly different. The drug solubility values obtained using propionic acid instead of carbomer are shown in Table VI.

Statistical Analysis of the Solubility Data

It was of interest to determine if the amount of surfactant in the reference gel B (PS=0.2, PX=0.2, HG=2) had resulted in a significant increase in drug solubility. Therefore, a student's t-test was performed to compare the solubility of drug in gel B to the solubility in the two gels without surfactant. These two gels were gel 3 (PS=0, PX=0, HG=2), and gel 10 (PS=0, PX=0, HG=0). The only difference between gels 3 and 10 were the concentration of hexylene glycol. The t-test (Table VII) indicated that the addition of surfactant had resulted in a significant increase in drug solubility. Eight gels had solubility values which were not significantly different from the reference gel. These gels were #5, 6, 11, 12, 13, 16, 17, and 18 which contained the highest level of surfactants (Table V).

TABLE VI

The Solubility of AGN in the Vehicle of the Various Formulated Gels (Propionic Acid Was Substituted for Carbomer)

| % Hexylene glycol | % Polysorbate 40 | % Poloxamer 407 | Solubility (mg/ml) |
|---|---|---|---|
| 0 | 0.0 | 0.0 | 0.0145 ± 0.0003 |
| 0 | 0.0 | 0.2 | 0.0679 ± 0.0044 |
| 0 | 0.0 | 0.4 | 0.0874 ± 0.0066 |
| 0 | 0.2 | 0.0 | 0.0523 ± 0.0027 |
| 0 | 0.2 | 0.2 | 0.0697 ± 0.0032 |
| 0 | 0.2 | 0.4 | 0.0800 ± 0.0040 |
| 0 | 0.4 | 0.0 | 0.0893 ± 0.0088 |
| 0 | 0.4 | 0.2 | 0.0775 ± 0.0008 |
| 0 | 0.4 | 0.4 | 0.0867 ± 0.0060 |
| 2 | 0.0 | 0.0 | 0.0209 ± 0.0017 |
| 2 | 0.0 | 0.2 | 0.0737 ± 0.009 |
| 2 | 0.0 | 0.4 | 0.0863 ± 0.0026 |
| 2 | 0.2 | 0.0 | 0.0759 ± 0.0035 |
| 2 | 0.2 | 0.2 | 0.0938 ± 0.0001 |
| 2 | 0.2 | 0.4 | 0.1020 ± 0.0029 |
| 2 | 0.4 | 0.0 | 0.0980 ± 0.0117 |
| 2 | 0.4 | 0.2 | 0.1300 ± 0.0062 |
| 2 | 0.4 | 0.4 | 0.1180 ± 0.0038 |

TABLE VII

Student's T-Test Comparing Drug Solubility in the Vehicle of the Prepared Gels to Solubility in Gel B

| Gels | Solubility (mg/ml) | Std. Dev. | P Value (2 TAIL) | Difference |
|---|---|---|---|---|
| 1 | 0.073700 | 0.00086 | 0.024822 | Significant |
| 2 | 0.075859 | 0.00351 | 0.040707 | Significant |
| 3 | 0.020875 | 0.00175 | 0.002689 | Significant |
| 5 | 0.086249 | 0.00257 | 0.113846 | Not significant |
| 6 | 0.097950 | 0.01165 | 0.974439 | Not significant |
| 7 | 0.069730 | 0.00321 | 0.024199 | Significant |
| 8 | 0.067890 | 0.00448 | 0.026539 | Significant |
| 9 | 0.052275 | 0.00268 | 0.008625 | Significant |
| 10 | 0.014465 | 0.00029 | 0.002079 | Significant |
| 11 | 0.087410 | 0.00660 | 0.231684 | Not significant |
| 12 | 0.089315 | 0.00087 | 0.163089 | Not significant |
| 13 | 0.102035 | 0.00292 | 0.414257 | Not significant |
| 14 | 0.129750 | 0.00615 | 0.030781 | Significant |
| 15 | 0.077475 | 0.00088 | 0.034515 | Significant |
| 16 | 0.080015 | 0.00395 | 0.064712 | Not significant |
| 17 | 0.075105 | 0.00381 | 0.040134 | Significant |
| 18 | 0.086680 | 0.00597 | 0.193570 | Not significant |
| Gel B | 0.097621 | 0.00536 | — | — |

The solubility data were also analyzed with the use of RS/Discover® software and response surface methodology (RSM). The goal was to find the combination of polysorbate 40, poloxamer 407, and hexylene glycol concentrations which led to maximum drug solubility (within the range of studied factors). Once the data for the factors and responses were entered into the worksheet, a model was fit to the data. Table VIII shows the least squares coefficients. From the table it is clear that two of the interaction terms involving hexylene glycol are not significant. Therefore, these two terms were eliminated. The least square coefficients for the refined model are shown in Table IX.

TABLE VIII

Least Squares Coefficients for Solubility

| Term | Coeff. | Std. Error | Significance |
|---|---|---|---|
| 1 | 76.911 | 2.122 | |
| PS | 17.140 | 2.599 | |
| PX | 13.896 | 2.599 | |
| HG | 7.438 | 2.122 | |
| PS*PX | −20.475 | 3.183 | 0.0001 |
| PS*HG | 3.190 | 2.599 | 0.2295 |
| PX*HG | −2.446 | 2.599 | 0.3545 |

TABLE IX

Least Squares Coefficients for Solubility (Refined Model)

| Term | Coeff. | Std. Error | Significance |
|---|---|---|---|
| 1 | 76.911 | 2.135 | |
| PS | 17.140 | 2.615 | |
| PX | 13.896 | 2.615 | |
| HG | 7.438 | 2.135 | 0.0015 |
| PS*PX | −20.475 | 3.203 | 0.0001 |

The model became simpler. The equation which fits the data is:

$$\text{Solubility} = 76.91 + 17.14\, PS + 13.90\, PX + 7.44\, HG - 20.48\, PS.PX$$

The residual values are the difference between the observed values and the fitted values of the response associated with the model. RS/Discover® automatically studentizes the residuals so that they have a constant variance of one. To check whether there is any relationship between the magnitude of the residuals and the fitted values of the response, a plot of absolute values of the studentized residuals versus the fitted values was constructed (FIG. 1). Any type of relationship may indicate the need to transform the response. The plot suggests that there is no clear trend in the residuals and the model does not need to be refined.

Figure 2:
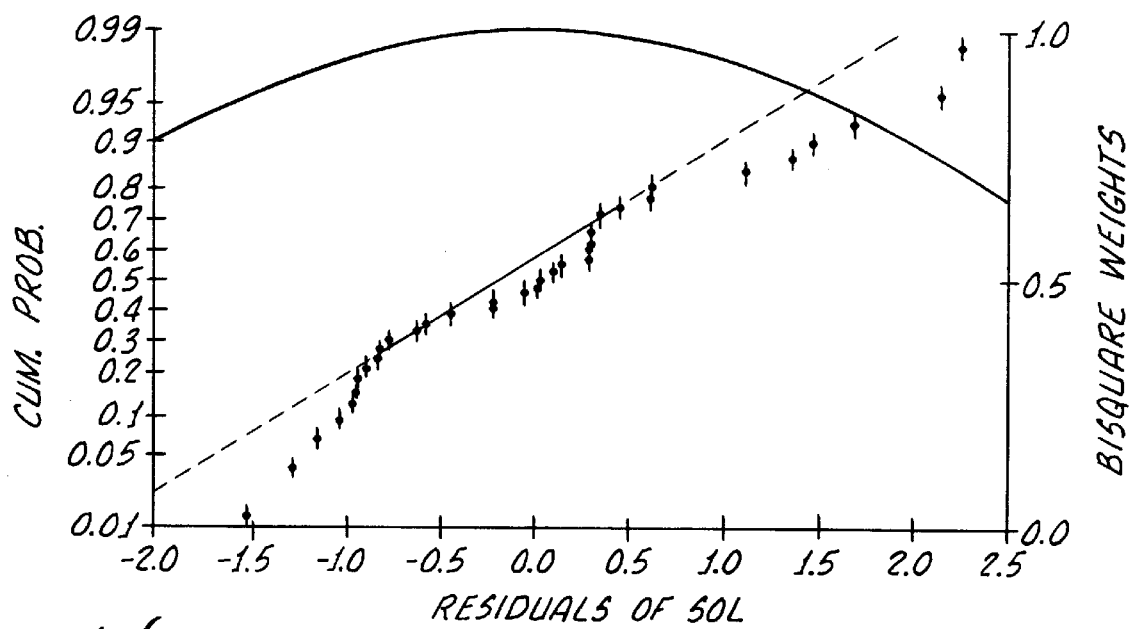
FIG. 2: Normal plot of residuals for the solubility data.

A normal probability plot of the residuals shown in FIG. 2 indicates that points on the plot fall very close to the line indicating that the model's residuals are normally distributed.

Figure 3:
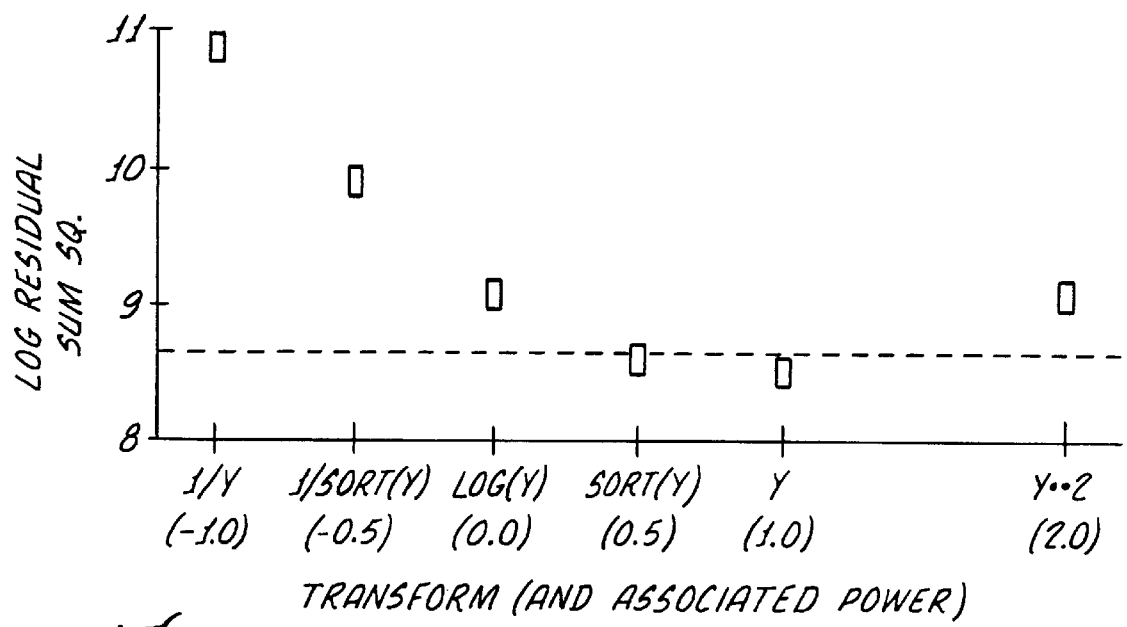
FIG. 3: Effect of transformation of the response (solubility data)

To determine if the model can be improved by transforming the response, the fit of the model is checked. RS/Discover® produces a graph indicating the possible transformations and their effects on the logarithm of the sum of squares of the residuals (FIG. 3). The transformation that results in the smallest value for this number produces the best fit. Transformations below the dashed line are within the 95% confidence interval for the best transformation. Since the untransformed response is below the line, the response was not transformed.

Figure 4:
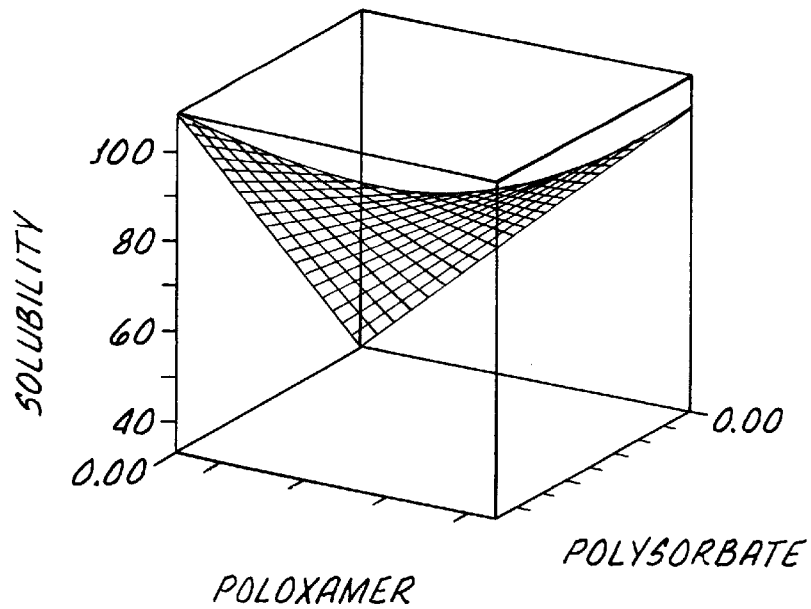
FIG. 4: Response surface fitting the solubility data (with hexylene glycol)
Figure 5:
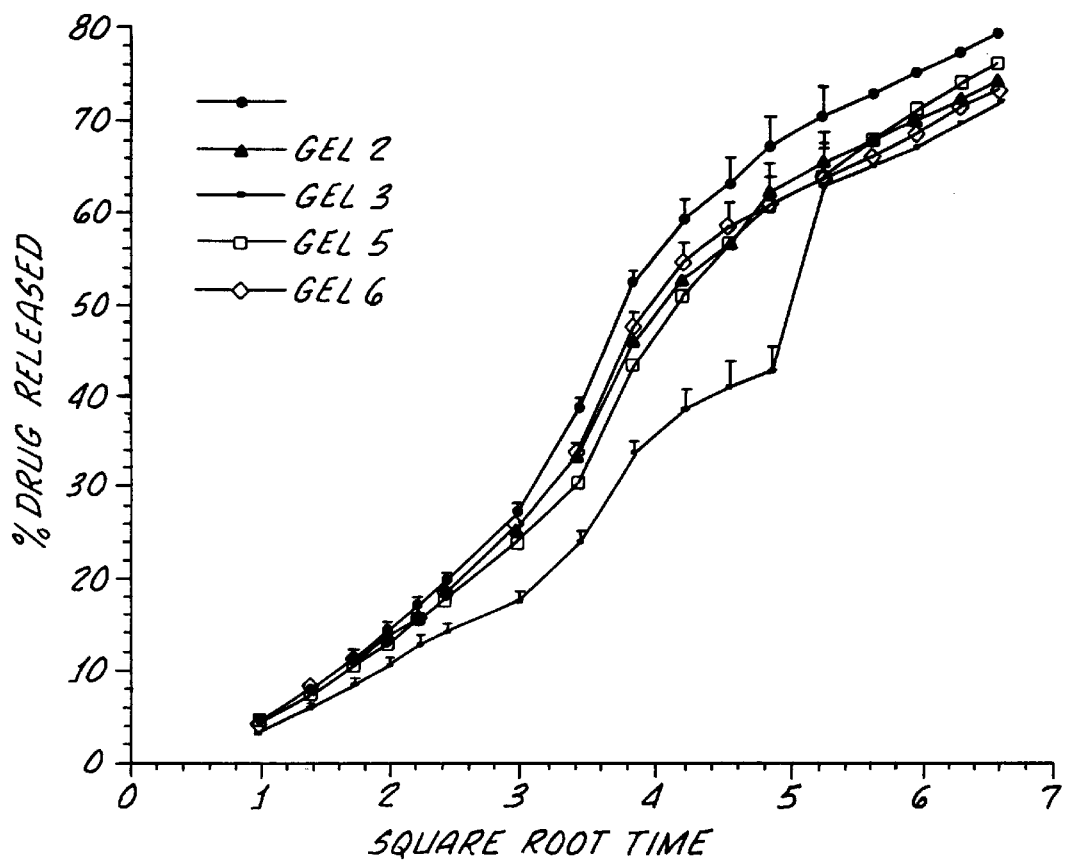
FIG. 5: Effect of square root of time on % drug released from gels 1 through 6.
Figure 6:
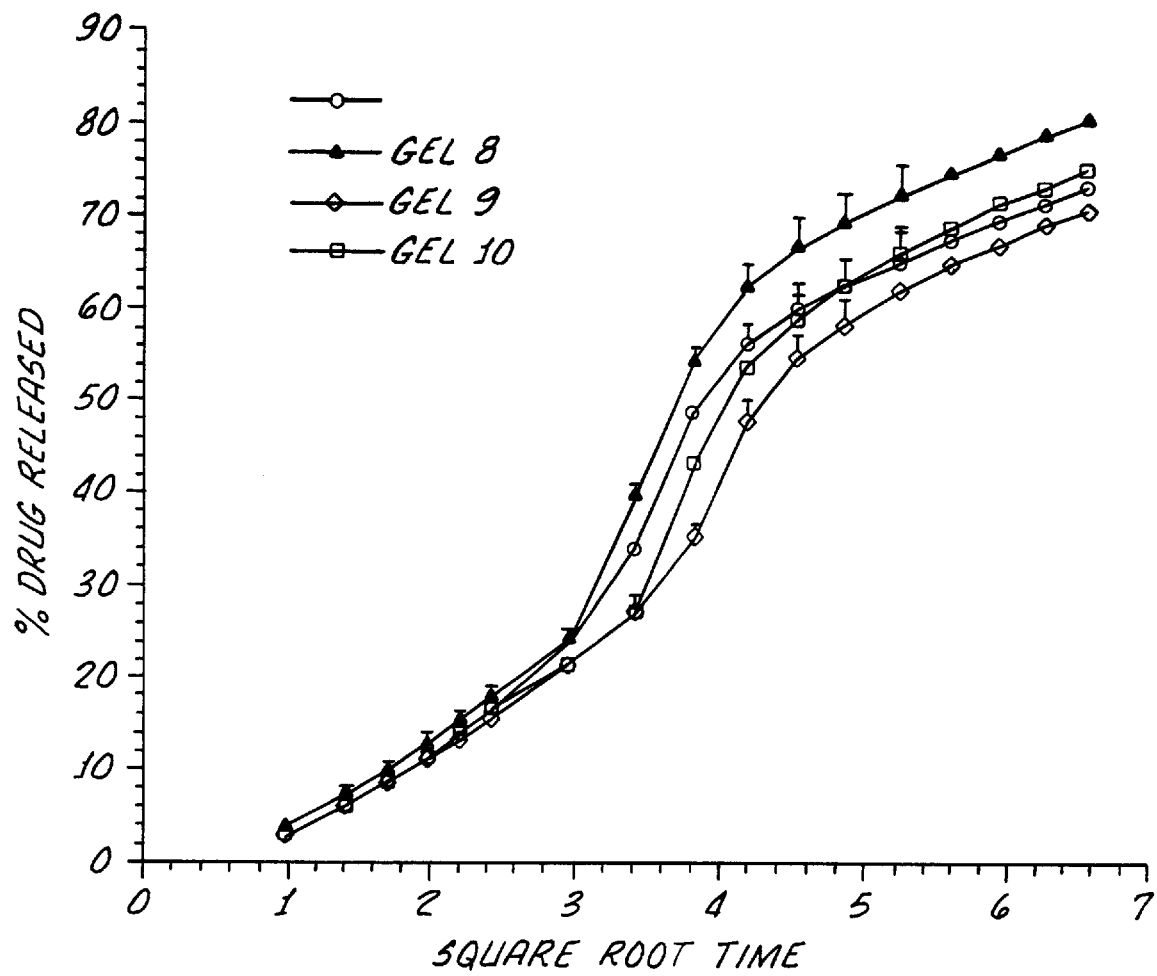
FIG. 6: Effect of square root of time on % drug released from gels 7 through 10.
Figure 7:
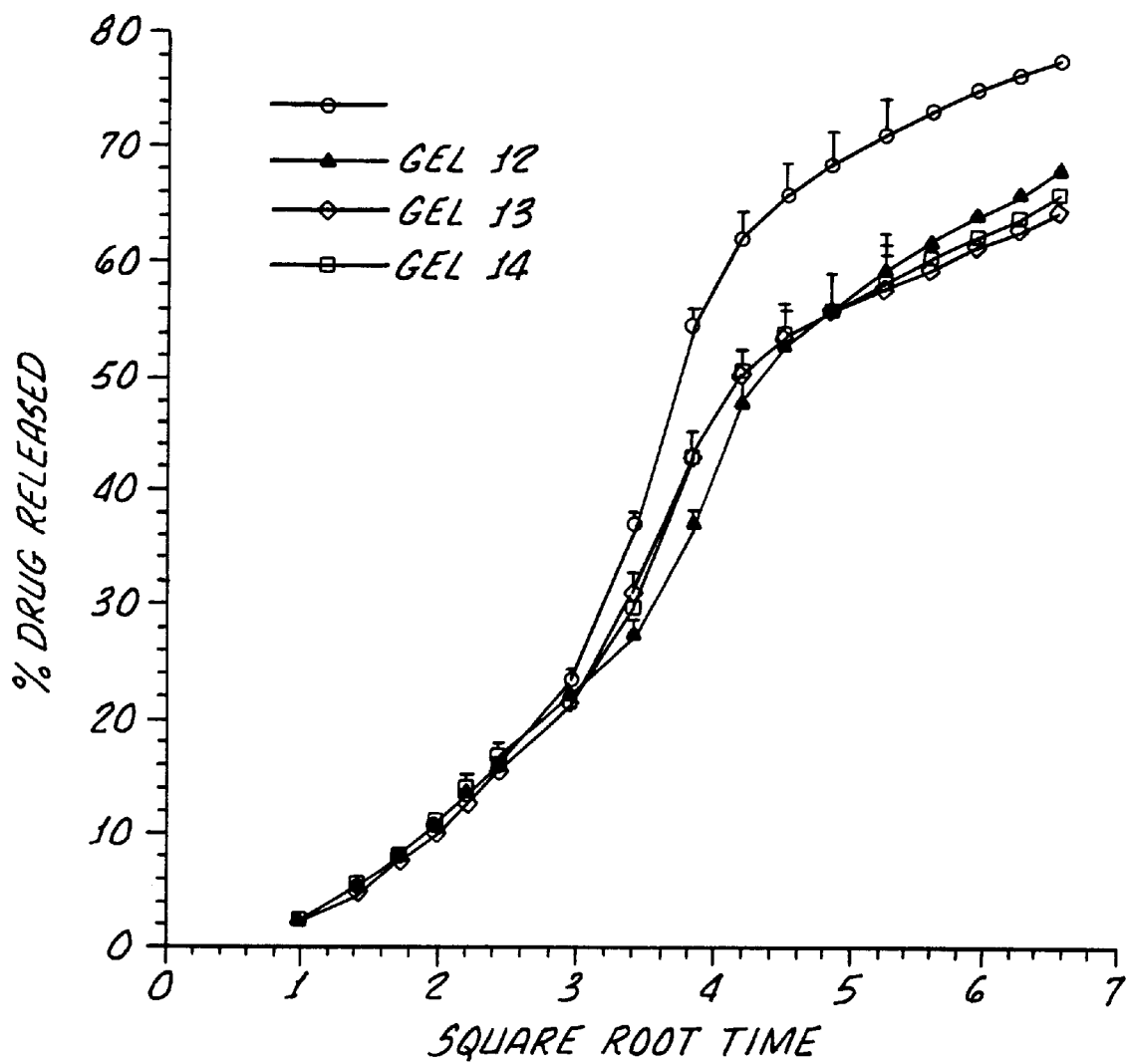
FIG. 7: Effect of square root of time on % drug released from gels 11 through 14.
Figure 8:
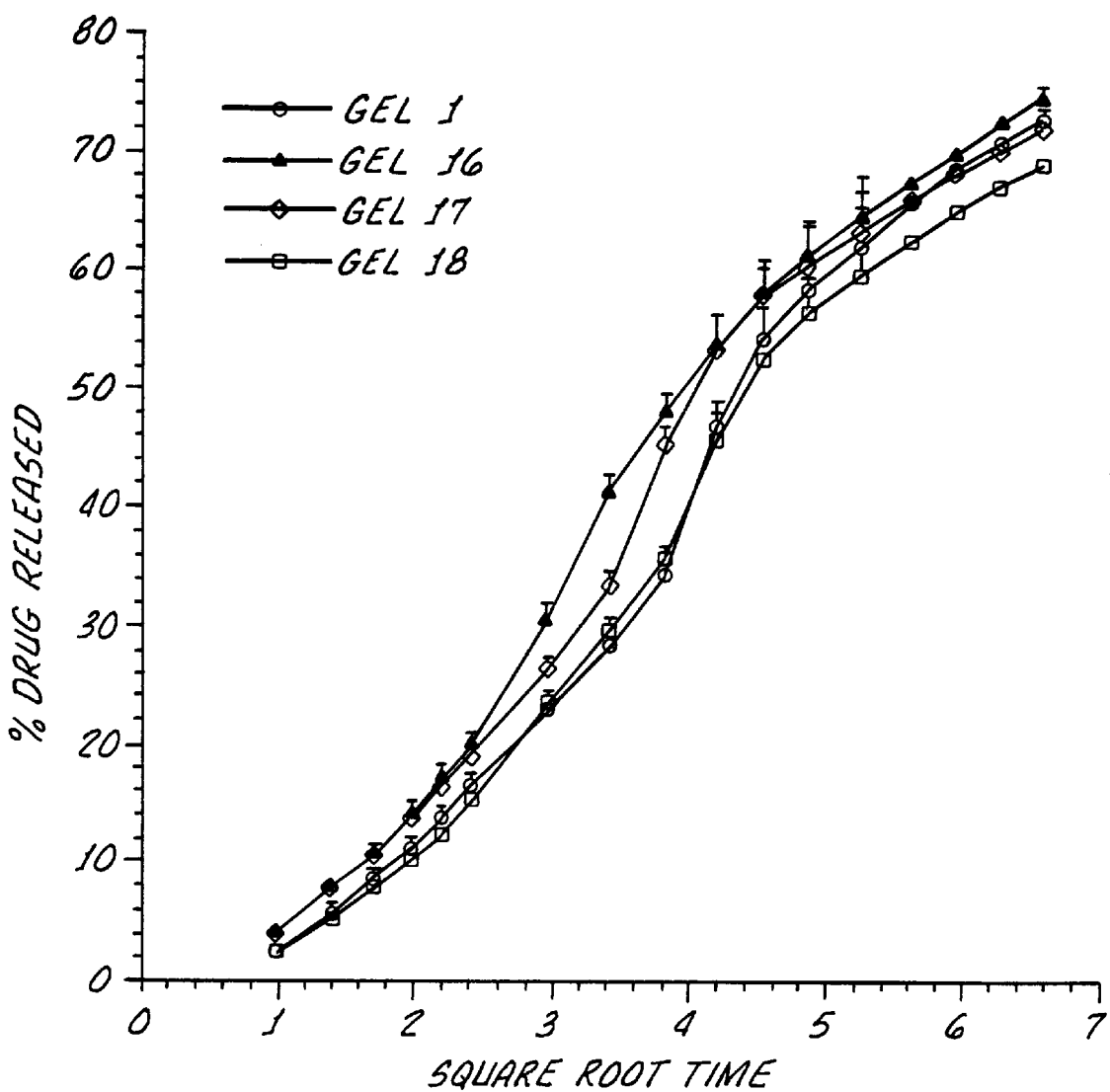
FIG. 8: Effect of square root of time on % drug released from gels 15 through 18.

A three-dimensional response surface is shown in FIG. 4. In order to determine the factor levels which result in maximum drug solubility, optimization was performed. As seen in Table X, when preparing a gel which contains between 0 to 0.4 polysorbate 40, poloxamer 407, and hexylene glycol, a maximum solubility of 103.17 μg/ml can be obtained with Polysorbate 40 at level 0.4, Poloxamer 407 at level 0.0, and hexylene glycol at level 2.

TABLE X

Optimization of Drug Solubility

| Factor | Range | Initial Setting | Optimal Value |
|---|---|---|---|
| Polysorbate 40 | 0 to 0.4 | 0.2 | 0.4 |
| Poloxamer 407 | 0 to 0.4 | 0.2 | 0.0 |
| Hexylene glycol | 0 to 2 | 2 | 2 |
| Response | | | |
| Solubility | Maximize | 97.6 μg/ml | 103.17 μg/ml |

In vitro Release of Gels

Drug release was studied from all seventeen formulated gels as described previously. The release profiles for each gel were an average of six runs, and were plotted as % Drug released vs. Square root of time. The release profiles for these gels are shown in FIGS. 5–8.

Release Studies of Prepared Gels

From the plots of % Drug Released vs. Square Root of Time, it is seen that the average amount of drug released from 200 mg of any of the formulations was approximately 70% over a 44 hour period. The highest release rate was observed for the prototype gel which contained 0.2% polysorbate 40, 0.2% Poloxamer 407, and 2% hexylene glycol. The lowest release rate was observed with gel 3 (PS=0, PX=0, HG=2). The average variability observed within each run was approximately 5.56%.

Slopes of the Release Profiles

In order to compare the release rates of drug from each formulation, the slope of the linear portion of the plot of % Drug released vs. Square root of time was computed for each of the 18 gels. The value of the calculated slopes are shown in Table XI. The slope for each plot was obtained as an average of six runs and based on a correlation coefficient $(R^2) > 0.94800$.

TABLE XI

Slope Values Calculated from the Release Profiles of the Formulated Gels

| Gel # | Concentration (PS, PX, HG) | Slope ± Std Dev. | $R^2$ |
|---|---|---|---|
| B | (0.2, 0.2, 2) | 13.5871 ± 0.9982 | 0.9904 |
| 1 | (0, 0.2, 2) | 11.3446 ± 0.2873 | 0.9483 |
| 2 | (0.2, 0, 2) | 10.1447 ± 0.7870 | 0.9950 |
| 3 | (0, 0, 2) | 7.4477 ± 0.2806 | 0.9924 |
| 5 | (0, 0.4, 2) | 9.9382 ± 0.9804 | 0.9958 |
| 6 | (0.2, 0, 2) | 12.0523 ± 1.5882 | 0.9833 |
| 7 | (0.2, 0.2, 0) | 11.9547 ± 1.3305 | 0.9517 |
| 8 | (0, 0.2, 0) | 10.1429 ± 0.5636 | 0.9947 |
| 9 | (0.2, 0, 0) | 10.0411 ± 0.0055 | 0.9841 |
| 10 | (0, 0, 0) | 9.9340 ± 0.3207 | 0.9954 |
| 11 | (0, 0.4, 0) | 10.3253 ± 0.1522 | 0.9809 |
| 12 | (0.4, 0, 0) | 10745 ± 0.4200 | 0.9922 |
| 13 | (0.2, 0.4, 2) | 9.6201 ± 0.1916 | 0.9869 |
| 14 | (0.4, 0.2, 2) | 11.4951 ± 0.3704 | 0.9869 |
| 15 | (0.4, 0.2, 0) | 11.1432 ± 0.2825 | 0.9928 |
| 16 | (0.2, 0.4, 0) | 10.8250 ± 1.1877 | 0.9920 |
| 17 | (0.4, 0.4, 2) | 11.8246 ± 0.5878 | 0.9872 |
| 18 | (0.4, 0.4, 0) | 11.4089 ± 0.6560 | 0.9798 |

Statistical Analysis of Slope Data

As with drug solubility, it was of interest to determine if the amount of surfactant in the reference gel B (PS=0.2, PX=0.2, HG=2) had resulted in a significant increase in drug release. Therefore, a student's t-test was performed to compare the release rate of drug in gel B to the release rate from the two gels without surfactant; gel 3 (PS=0, PX=0, HG=2), and gel 10 (PS=0, PX=0, HG=0). The t-test (Table XII) indicated that the addition of surfactant had resulted in a significant increase in the release of the drug from gel B. In addition, the t-test revealed that the release of drug from the reference gel was significantly higher than most gels except gel 6 (0.4,0,2), gel 7 (0.2,0.2,0), and gel 17 (0.4,0.4,2).

TABLE XII

Student's t-test Comparing Drug Release (Slopes) from the Prepared Gels to Release from Gel B

| GELS | Slope | Std Dev. | R2 | P value (2 TAIL) | Difference |
|---|---|---|---|---|---|
| 1 | 11.3446 | 0.28734 | 0.94829 | 0.002510 | Significant |
| 2 | 10.1447 | 0.78707 | 0.98923 | 0.001860 | Significant |
| 3 | 7.4477 | 0.28062 | 0.98156 | 0.000002 | Significant |
| 5 | 9.9382 | 0.98045 | 0.99042 | 0.000440 | Significant |
| 6 | 12.0523 | 1.58828 | 0.98332 | 0.138900 | Not significant |
| 7 | 11.9547 | 1.33048 | 0.95172 | 0.103840 | Not significant |
| 8 | 10.1429 | 0.56364 | 0.99466 | 0.003750 | Significant |
| 9 | 10.0411 | 0.00545 | 0.98414 | 0.002780 | Significant |
| 10 | 9.3390 | 0.32071 | 0.99544 | 0.002530 | Significant |
| 11 | 10.3253 | 0.15223 | 0.98089 | 0.004220 | Significant |
| 12 | 10.2745 | 0.41097 | 0.99225 | 0.004210 | Significant |
| 13 | 9.6201 | 0.19163 | 0.98692 | 0.001610 | Significant |
| 14 | 11.4952 | 0.37036 | 0.98685 | 0.029800 | Significant |
| 15 | 11.1432 | 0.28253 | 0.99282 | 0.015770 | Significant |
| 16 | 10.8251 | 1.18767 | 0.99196 | 0.004400 | Significant |
| 17 | 11.8246 | 0.58781 | 0.98720 | 0.057890 | Not significant |
| 18 | 11.4089 | 0.65602 | 0.97977 | 0.028520 | Significant |
| Gel B | 13.5871 | 0.99825 | 0.99043 | — | — |

Next, the release data obtained from all the gels were analyzed using RS/Discover® software and response surface methodology (RSM). The goal was to find the combination of Polysorbate 40, Poloxamer 407, and hexylene glycol concentrations which led to maximum drug release within the range of studied factors.

A model containing interaction terms was fit to the release data. The equation is shown below. Table XIII shows the least squares coefficients.

$$\text{Slope} = 10.94 + 0.88\,PS + 0.38\,PX + 0.30\,HG - 0.42\,PS.PX + 0.48\,PS.HG + 0.04\,PX.HG$$

TABLE XIII

Least Squares Coefficients for Release Rate

| Term | Coeff. | Std. Error | Significance |
|---|---|---|---|
| 1 | 10.942 | 0.2174 | |
| PS | 0.884 | 0.2442 | |
| PX | 0.379 | 0.2648 | |
| HG | 0.304 | 0.2174 | |
| PS*PX | -0.424 | 0.3440 | 0.2239 |
| PS*HG | 0.480 | 0.2842 | 0.0983 |
| PX*HG | 0.0438 | 0.2648 | 0.8695 |

From the Table it is observed that the interaction coefficients were not significant. Therefore, it was decided to divide the drug release data into two categories based on the amount of hexylene glycol present in the gels (HG=0 vs. HG=2). Each group was analyzed separately.

First, the release data from the nine gels not containing hexylene glycol were analyzed. A quadratic model was used to fit the release data. Table XIV shows the least squares coefficients. The equation is shown below:

$$\text{Slope} = 11.29 + 0.40\,PS + 0.34\,PX + 0.19\,PS.PX - 0.31\,PS^2 - 0.66\,PX^2$$

TABLE XIV

Least Squares Coefficients for Release Rate Data (Gels not Containing Hexylene Glycol)

| Term | Coeff. | Std. Error | Significance |
|---|---|---|---|
| 1 | 11.286 | 0.4336 | |
| PS | 0.404 | 0.2482 | |
| PX | 0.338 | 0.2278 | |
| PS*PX | 0.185 | 0.3040 | 0.5511 |
| $PS^2$ | -0.309 | 0.3820 | 0.4297 |
| $PX^2$ | -0.659 | 0.4184 | 0.1348 |

As seen from the table, the interaction terms are not significant. Eliminating these terms leads to a linear model which does not fit the data well. This indicates that there is not sufficient data within the ranges studied to fit a suitable model. The equation which fits the data is:

$$\text{Slope} = 11.29 + 0.40\,PS + 0.34\,PX$$

The release data obtained from gels containing hexylene glycol at 2% were also fit using a quadratic model. The least squares coefficients are shown in Table XV.

It is observed that all the interaction terms are significant. The equation which fits the data is:

$$\text{Slope} = 13.20 + 1.16\,PS + 0.28\,PX - 0.88\,PS.PX - 1.02\,PS^2$$

TABLE XV

Least Squares Coefficients for Release Rate Data (Gels Containing 2% Hexylene Glycol)

| Term | Coeff. | Std. Error | Significance |
|---|---|---|---|
| 1 | 13.196 | 0.3977 | |
| PS | 1.160 | 0.2874 | |
| PX | 0.282 | 0.2857 | |
| PS*PX | -0.878 | 0.3453 | 0.0179 |
| $PS^2$ | 0.025 | 0.3484 | 0.0314 |
| $PX^2$ | -2.311 | 0.4365 | 0.0001 |

Figure 9:
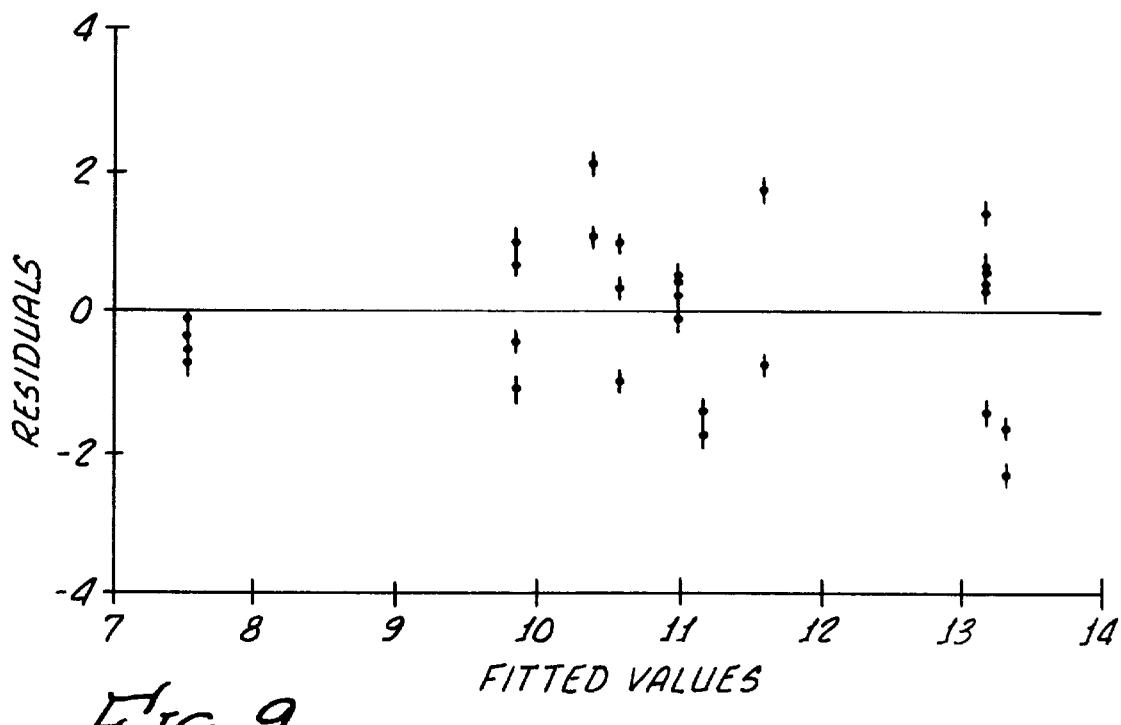
FIG. 9: Plot of residuals vs. fitted values for the release data.

To determine whether there is any relationship between the magnitude of the residuals and the fitted values of the response, a plot of absolute values of the studentized residuals versus the fitted values was constructed (FIG. 9). The plot suggests that there is no clear trend in the residuals and the model does not need to be refined.

Figure 10:
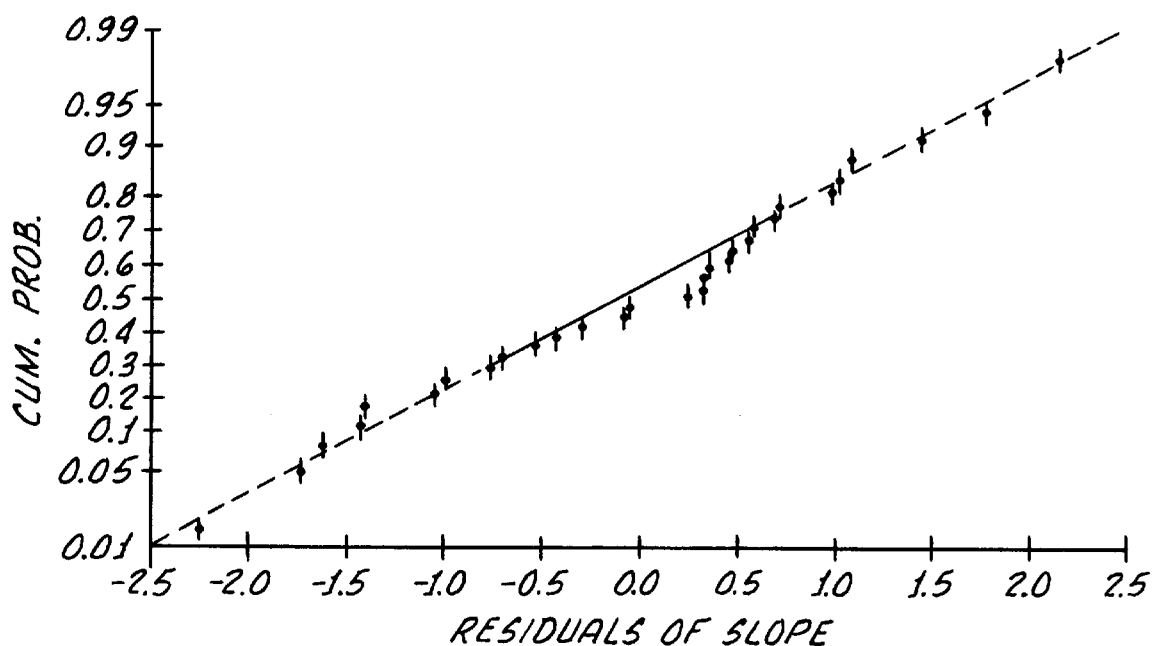
FIG. 10: Normal plot of residuals for the release data.

A normal probability plot of the residuals shown in FIG. 10 indicates that points on the plot fall very close to the line indicating that the model's residuals are normally distributed.

Figure 11:
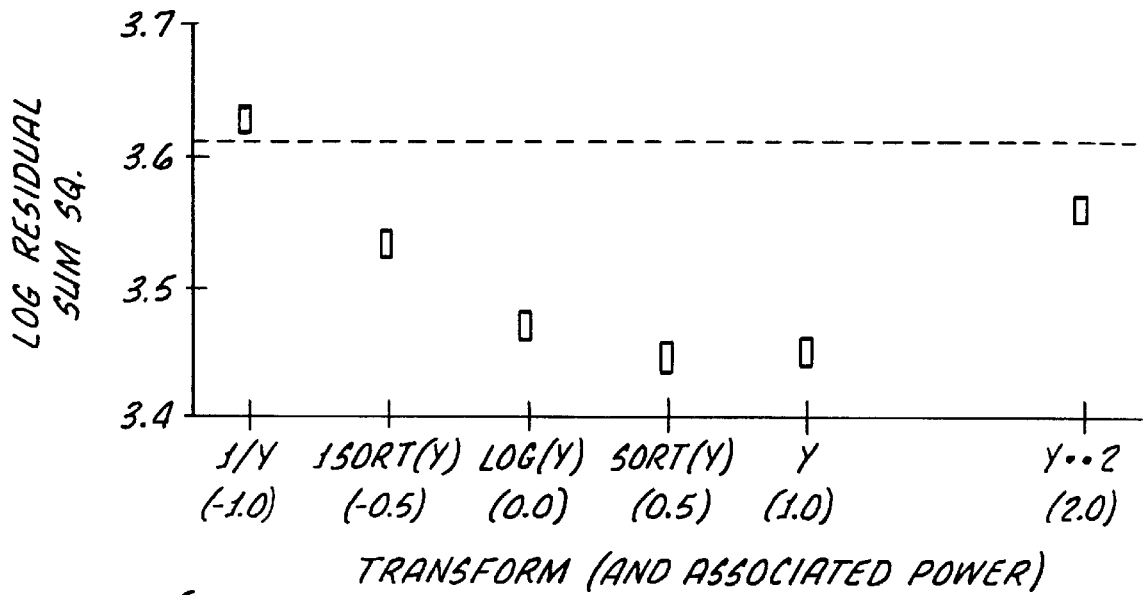
FIG. 11: Effect of transformation of the response (release data)

To determine if the model can be improved by transforming the response, the fit of the model is checked. The graph showing the possible transformations and their effects on the logarithm of the sum of squares of the residuals is shown in FIG. 11. Transformations below the dashed line are within the 95% confidence interval for the best transformation. Since the untransformed response is below the line, the response is not transformed.

Figure 12:
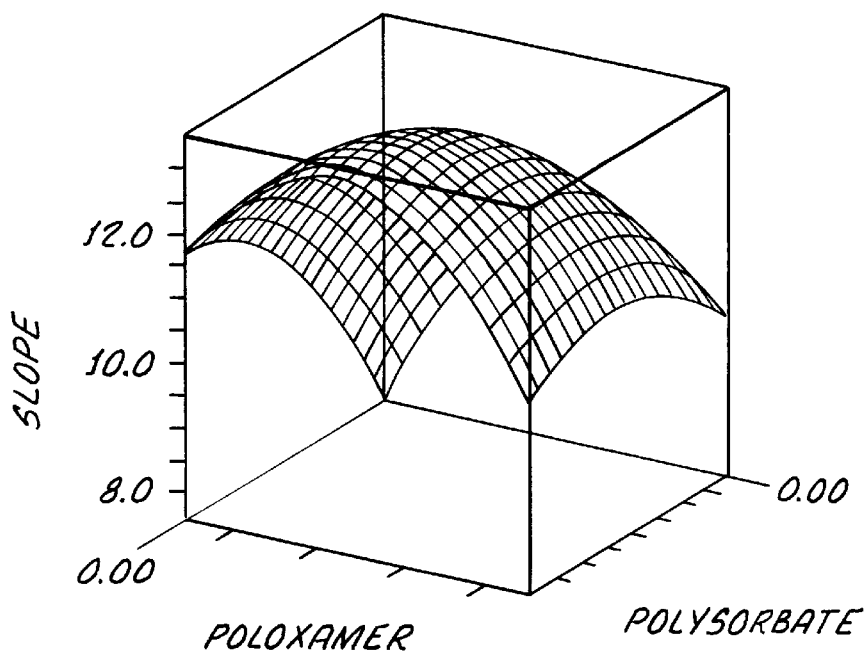
FIG. 12: Response surface fitting the release data (with hexylene glycol)

A three dimensional plot showing the effect of polysorbate 40 and Poloxamer 407 (when HG=2) on slope is shown in FIG. 12.

In order to determine the levels of surfactants which result in maximum drug release rate, optimization is performed. As seen in Table XVI, when preparing a gel which contains between 0 to 0.4% polysorbate 40 and poloxamer 407, and 0 to 2% hexylene glycol, a slope of 13.53 can be obtained with 0.32% polysorbate 40, 0.18% poloxamer 407, and 2% hexylene glycol.

TABLE XVI

Optimization of Drug Release Rate

| Factor | Range | Initial Setting | Optimal Value |
|---|---|---|---|
| Polysorbate 40 | 0 to 0.4 | 0.2 | 0.32 |
| Poloxamer 407 | 0 to 0.4 | 0.2 | 0.18 |
| Response | | | |
| Slope | Maximize | 13.59 | 13.53 |

Correlation Between Solubility and Release

Figure 13:
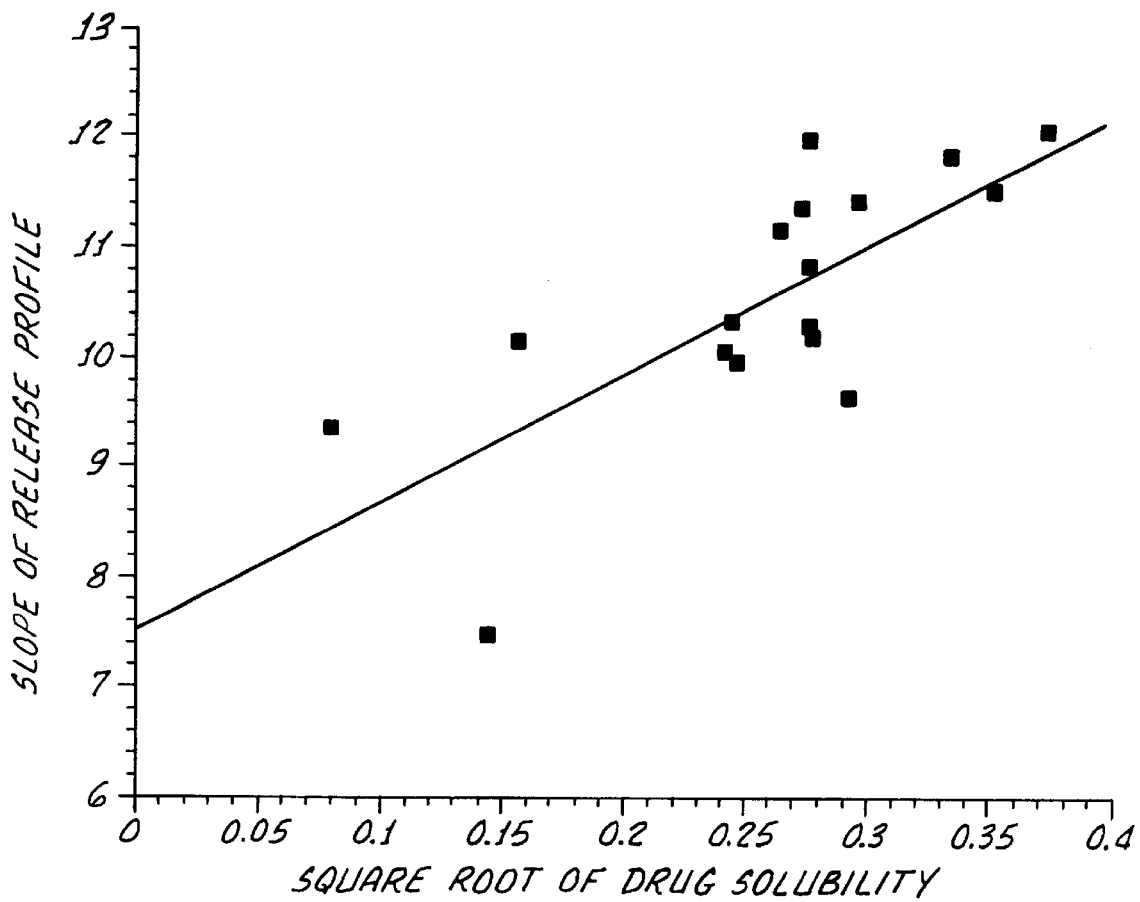
FIG. 13: Correlation between release rate of drug from gels and the square root of drug solubility.

In order to investigate a possible correlation between drug solubility and the rate of drug release, a plot of slope of release profile vs. square root of solubility of drug in gel was constructed. The highest correlation coefficient obtained was 0.5553 which was for drug solubility in solutions without carbomer or base (FIG. 13). Therefore, it was concluded that within the range of surfactant and cosolvent studied there was no correlation observed between drug release and solubility.

Maximizing Solubility and Release

The final statistical analysis involved the simultaneous optimization of the two responses studied; drug solubility and release rate. This analysis was performed in order to identify the concentration of the two surfactants and cosolvent which could be used in producing a gel with maximum solubility and release. RS/Discover® does not perform simultaneous optimizations, however it is possible to optimize one of the responses while constraining the range of the other response. This is an iterative process.

For this purpose, slope was maximized while the range of solubility was constrained. The results of the process are shown in Table XVII. It was concluded that a maximum slope of 12.02 can be obtained by preparing a gel containing 0.4% polysorbate 40, 0.0% poloxamer 407, and 2% hexylene glycol. The range of drug solubility in this gel is calculated to be between 102 to 108 µg/ml.

TABLE XVII

Simultaneous Optimization of Drug Solubility and Release Rate

| Factor | Range | Initial Setting | Optimal Value |
|---|---|---|---|
| Polysorbate 40 | 0 to 0.4 | 0.2 | 0.4 |
| Poloxamer 407 | 0 to 0.4 | 0.2 | 0.0 |
| Hexylene glycol | 0 to 2 | 2 | 2 |
| Response | | | |
| Slope | Maximize | 13.59 | 12.02 |
| Solubility | 102 to 108 µg/ml | 97.6 µg/ml | 107.99 µg/ml |

Effect of Drug Particle Solubility on Drug Release

From the solubility data indicated in Table VII it is apparent that approximately 90% of the drug is present in the aqueous based gel in the form of solid particles. In order to determine if the rate of dissolution of the particles is limiting the rate of drug release, the data obtained from the in vitro release study was analyzed (Table XVIII). From the data it is observed that the rate of drug release remains constant even after three hours, beyond the point where 10% of the drug (the total amount of drug saturating the aqueous gel) is released. Therefore, it is concluded that the solubility of the drug particles in the gel is not rate limiting.

TABLE XVIII

The Amount of Drug Released at Given Time Intervals (0.1% AGN Gel, formula 8606X, Lot# 10169)

| Time (hr) | Amount Released (mg) | % Drug Released |
|---|---|---|
| 1 | 0.00725 ± 0.0005 | 3.6259 |
| 2 | 0.00690 ± 0.0005 | 7.0805 |
| 3 | 0.00626 ± 0.0004 | 10.2129 |
| 4 | 0.00624 ± 0.0004 | 13.3310 |
| 5 | 0.00600 ± 0.0003 | 16.3225 |
| 6 | 0.00570 ± 0.0002 | 19.1727 |
| 7 | 0.00551 ± 0.0003 | 21.9270 |
| 8 | 0.00526 ± 0.0003 | 24.5573 |
| 9 | 0.00496 ± 0.0004 | 27.0367 |
| 12 | 0.02378 ± 0.0024 | 38.9273 |
| 15 | 0.01727 ± 0.0018 | 47.5600 |
| 18 | 0.00901 ± 0.0009 | 52.0643 |
| 21 | 0.00582 ± 0.0006 | 54.9760 |

Effect of Membrane on Drug Release

Figure 14:
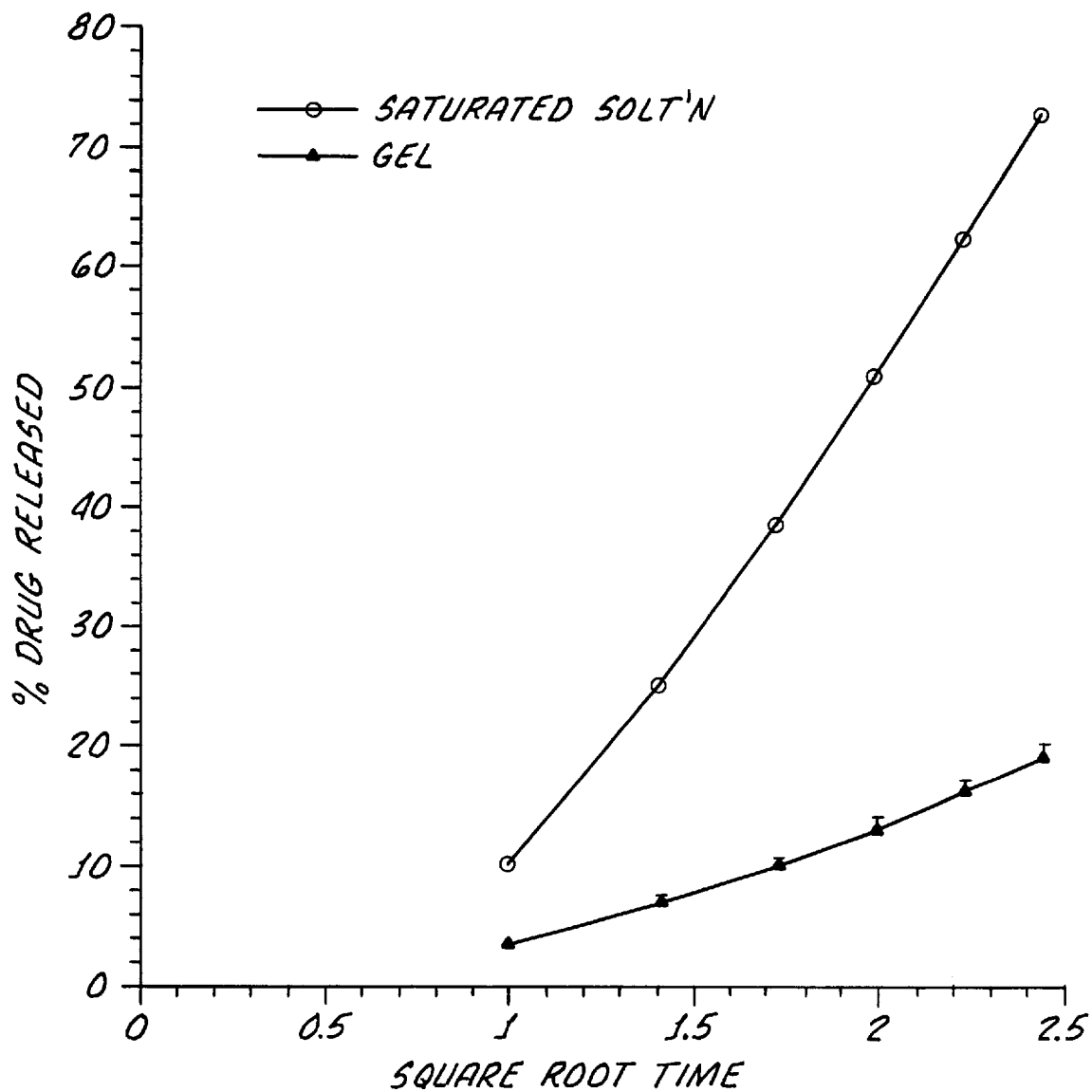
FIG. 14: Release profiles comparing drug release from the prototype gel (H) to drug release from a saturated solution.

In order to investigate the possibility of the silicone membrane being rate limiting, the slope of the release profile for drug diffusion through the gel was compared to the slope of the release profile obtained from a saturated solution of the drug (FIG. 14). The slope of the linear portion of the curve for the gel was 13.587±0.973, and the slope obtained from the saturated solution was 46.652±0.998 indicating that drug release from the saturated solution was much higher than drug release through the gel. Therefore, this membrane was found to serve as a suitable support membrane offering no resistance to the diffusion of the drug.

Effect of Drug Concentration on Release Rate

Figure 15:
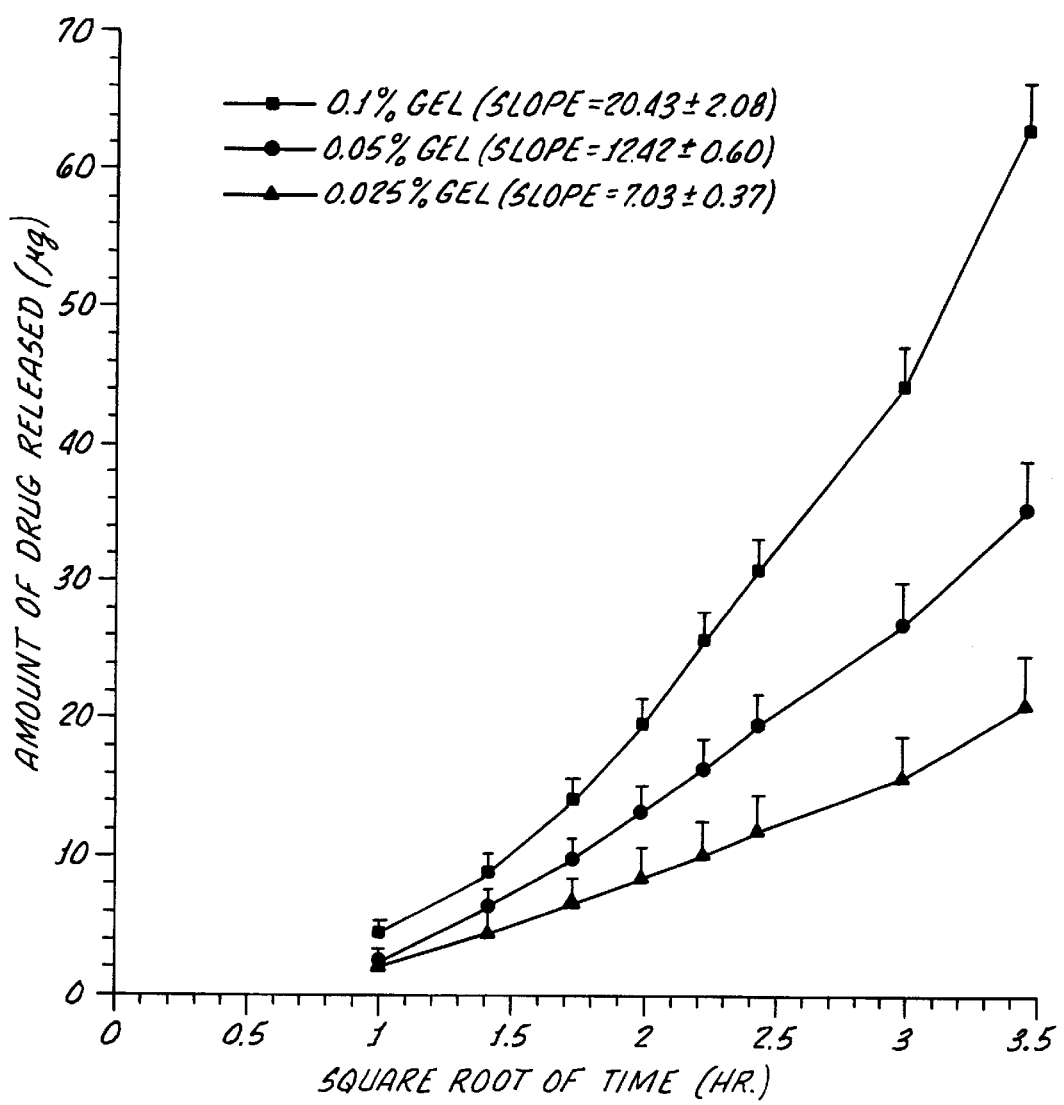
FIG. 15: Release profiles showing the effect of increasing the concentration of drug in the gel vehicle on the release rate, 0.025%, 0.05%, and 0.1%.

The results of the drug release study using 0.1%, 0.05%, and 0.025% have shown that drug release from the gel containing 0.1% is approximately 60% higher than the release of drug from the 0.05% gel, while drug release from the 0.05% gel is also 60% higher than the 0.025% gel (FIG. 15). Therefore, the in vitro release method has distinguished changes in drug release due to changes in drug concentration. Also, the results indicate that the drug release from the gel is more similar to drug release from solution, since drug release from suspensions containing twice as much drug is expected to provide only 40% increase in drug release rate (according to Higuchi's theory).

Conclusion

The effect of varying the concentrations of polysorbate 40, poloxamer 407, and hexylene glycol on the release and solubility of AGN in a gel indicated that the gel exhibited maximum solubility and release of the drug, AGN. This gel contained 0.2% polysorbate 40, 0.2% poloxamer 407, and 2% hexylene glycol. In addition, another gel was also identified which exhibited drug solubility and drug release that were not significantly different from the prototype gel. This second gel (gel 6) contained 0.4% polysorbate 40 and 2% hexylene glycol, but did not contain poloxamer. All other ingredients were available at the same concentration for both gels.

Although there has been hereinabove described a stable gel formulation and method suitable for application in topical treatment of acne and psoriasis, in accordance with the present invention, for the purpose of illustrating the manner in which the invention may be used to advantage, it should be appreciates that the invention is not limited thereto. Accordingly, any and all modifications, variations, or equivalent arrangements which may occur to those skilled in the art, should be considered to be within the scope of the present invention as defined in the appended claims.

What is claimed is:

1. A stable gel formulation for topical treatment of both acne and psoriasis comprising an effective amount of a compound having the formula Ethyl-6-[2-(4,4-1dimethylthiochroman-6-yl)-ethynyl]nicotinate in a pharmaceutical carrier comprising:
   (a) water;
   (b) edetate disodium;
   (c) ascorbic acid;
   (d) Carbomer 934P;
   (e) Poloxamer 407;
   (f) polyethylene glycol;
   (g) Polysorbate 40;
   (h) hexylene glycol;
   (i) butylated hydroxytoluene;
   (j) butylated hydroxyanisole;
   (k) benzyl alcohol: and
   (l) tromethamine
   wherein the Polysorbate 40 is present in an amount up to about 0.4% by weight, Poloxamer 407 is present in an amount up to about 0.4% by weight, and hexylene glycol is present in an amount up to about 2% by weight.

2. The formulation according to claim 1, wherein the Polysorbate 40 is present in an amount of about 0.32% by weight, the Poloxamer 407 is present in an amount of about 0.18% by weight, and the hexylene glycol is present in an amount of about 2% by weight.

3. A method for preparation of a formulation for topical treatment of both acne and psoriasis comprising the steps of:
   1) mixing purified water, edetate disodium, ascorbic acid and Carbomer 934P until the carbomer is dispersed to form a part I;
   2) mixing purified water, Poloxamer 407 to form a part II;
   3) adding part II to part I and homogenizing part I and part II;
   4) mixing polyethylene glycol, Polysorbate 40, hexylene glycol, butylated hydroxytoluene and butylated hydroxyanisole and heating to dissolve same;
   5) cooling the mixture of step 4) to room temperature and adding benzyl alcohol and Ethyl-6-[2-(4,4-dimethylthiochroman-6-yl] nicotinate thereto to form a part III;
   6) mixing purified water and tromethamine to form part IV;
   7) adding part III to parts I and II while stirring and thereafter adding part IV with mixing until homogeneous, said Polysorbate 40 being present in the formulation in an amount up to about 0.4% by weight, said Poloxamer 407 being present in the formulation in an amount up to about 0.4% by weight, and said hexylene glycol being present in the formulation in an amount up to about 2% by weight.

4. The formulation according to claim 3 wherein the Polysorbate 40 is present in an amount of about 0.32% by weight, the Poloxamer 407 is present in an amount of about 0.18% by weight, and the hexylene glycol is present in an amount of about 2% by weight.

5. A stable gel formulation for topical treatment of skin conditions in humans, said stable gel formulation comprising:
   an active agent having activity for treatment of acne and psoriasis, said active agent comprising:
   Ethyl-6-[2-(4,4-dimethylthiochroman-6-yl)-ethynyl] nicotinate; and
   nonaqueous vehicles for both solubilizing said active agent and forming a gel therewith, said nonaqueous vehicles enabling topical application of the gel to a skin condition, said vehicles each being present in amounts, and in combination, to control release of the active agent from the gel to the skin condition, said nonaqueous vehicles comprising Polysorbate 40, Poloxamer 407 and hexylene glycol, said Polysorbate 40 being present in an amount up to about 0.4% by weight, said Poloxamer 407 being present in an amount up to about 0.4% by weight and said hexylene glycol being present in an amount up to about 2% by weight.

6. A stable gel formulation for topical treatment of skin conditions in humans, said stable gel formulation comprising:
   an active agent having activity for treatment of acne and psoriasis, said active agent comprising:
   Ethyl-6-[2-(4,4 dimethylthiochroman-6-yl)-ethynyl] nicotinate; and
   nonaqueous vehicles for both solubilizing said active agent and forming a gel therewith, said nonaqueous vehicles enabling topical application of the gel to a skin condition, said vehicles each being present in amounts, and in combination, to control solubility of the active agent in the gel, said nonaqueous vehicles comprising Polysorbate 40, Poloxamer 407 and hexylene glycol, said Polysorbate 40 being present in an amount up to about 0.4% by weight, said Poloxamer 407 being present in an amount up to about 0.4% by weight and said hexylene glycol being present in an amount up to about 2% by weight.

7. A stable gel formulation for topical treatment of skin conditions in humans, said stable gel formulation comprising:
   an active agent having activity for treatment of acne and psoriasis, said active agent comprising:
   Ethyl-6-[2-(4,4 dimethylthiochroman-6-yl)-ethynyl] nicotinate; and
   nonaqueous vehicles for both solubilizing said active agent and forming a gel therewith, said nonaqueous vehicles enabling topical application of the gel to a skin condition, said vehicles each being present in amounts, and in combination, to control both solubility of the active agent in the gel and the release of the active agent from the gel to the skin condition, said nonaqueous vehicles comprising Polysorbate 40, Poloxamer 407 and hexylene glycol, said polysorbate 40 being present in an amount up to about 0.4% by weight, said poloxamer 407 being present in an amount up to about 0.4% by weight and said hexylene glycol being present in an amount up to about 2% by weight.

8. The formulation according to claim 7 wherein the Polysorbate 40 is present in an amount of about 0.32% by weight, the Poloxamer 407 is present in an amount of about 0.18% by weight, and the hexylene glycol is present in an amount of about 2% by weight.

* * * * *